(12) United States Patent
Sweeney (10) Patent No.: US 7,766,968 B2
(45) Date of Patent: Aug. 3, 2010

(54) MODULAR CANNULATED TOTAL JOINT PROSTHESIS

(76) Inventor: Patrick J. Sweeney, 1711 Pinehurst La., Flossmoor, IL (US) 60422

( * ) Notice: Subject to any disclaimer, the term of this patent is extended or adjusted under 35 U.S.C. 154(b) by 0 days.

(21) Appl. No.: 10/730,606

(22) Filed: Dec. 8, 2003

(65) Prior Publication Data
US 2005/0125067 A1    Jun. 9, 2005

(51) Int. Cl.
*A61F 2/40* (2006.01)
(52) U.S. Cl. .................................................. 623/19.11
(58) Field of Classification Search ... 623/19.11–22.19, 623/22.42–22.46, 23.15, 23.21, 23.22, 23.14, 623/22.4
See application file for complete search history.

(56) References Cited

U.S. PATENT DOCUMENTS

| | | | |
|---|---|---|---|
| 4,624,673 A | | 11/1986 | Meyer |
| 4,919,670 A | * | 4/1990 | Dale et al. ............... 623/19.14 |
| 4,995,883 A | | 2/1991 | Demane et al. |
| 5,181,928 A | | 1/1993 | Bolesky et al. |
| 5,282,865 A | * | 2/1994 | Dong ...................... 623/19.14 |
| 5,286,260 A | | 2/1994 | Bolesky et al. |
| 5,370,706 A | | 12/1994 | Bolesky et al. |
| 5,375,956 A | * | 12/1994 | Pennig ........................ 411/389 |
| 5,489,309 A | | 2/1996 | Lackey et al. |
| 5,507,830 A | | 4/1996 | DeMane et al. |
| 5,549,706 A | | 8/1996 | McCarthy |
| 5,702,480 A | | 12/1997 | Kropf et al. |
| 5,702,486 A | | 12/1997 | Craig et al. |
| 5,858,020 A | * | 1/1999 | Johnson et al. .......... 623/23.15 |
| 5,876,459 A | | 3/1999 | Powell |
| 5,888,206 A | | 3/1999 | Lob et al. |
| 5,906,644 A | | 5/1999 | Powell |
| 5,961,555 A | * | 10/1999 | Huebner .................. 623/19.11 |
| 6,197,063 B1 | | 3/2001 | Dews |
| 6,238,436 B1 | | 5/2001 | Lob et al. |
| 6,428,578 B2 | | 8/2002 | White |
| 6,524,342 B1 | * | 2/2003 | Muhlhausler et al. .... 623/19.14 |
| 6,716,250 B2 | * | 4/2004 | Ganjianpour ............ 623/22.42 |
| 2001/0011193 A1 | * | 8/2001 | Nogarin .................... 623/19.14 |
| 2001/0037152 A1 | | 11/2001 | Rockwood, Jr. |

(Continued)

FOREIGN PATENT DOCUMENTS

EP    1 093 777 B1    4/2001

(Continued)

OTHER PUBLICATIONS

"The Modular Advantage: A Comparison of Stem/Sleeve Modularity Versus One-Piece Stems in Total Hip Arthroplasty," Sep. 2005 Supplement to Orthopedics, 100 pages, vol. 28, No. 9, Slack Incorporated, Thorofare, NJ.

(Continued)

*Primary Examiner*—Alvin J Stewart
(74) *Attorney, Agent, or Firm*—Foley & Lardner LLP (57) ABSTRACT

A modular joint prosthesis is intended for implantation in a patient. According to an exemplary embodiment, the modular joint prosthesis includes a head and a stem coupled to the head. The stem has a proximal portion coupled to the head and a distal portion configured to extend into a long bone of the patient. The distal portion may be removed from the stem after implantation of the prosthesis without also removing the proximal portion.

8 Claims, 9 Drawing Sheets

U.S. PATENT DOCUMENTS

| | | |
|---|---|---|
| 2002/0004685 A1 | 1/2002 | White |
| 2002/0038148 A1 | 3/2002 | Fernandez et al. |
| 2002/0045950 A1 | 4/2002 | Draenert |
| 2002/0133234 A1 | 9/2002 | Sotereanos |
| 2002/0151984 A1 | 10/2002 | White |
| 2002/0177901 A1 | 11/2002 | Howie |
| 2002/0183849 A1 | 12/2002 | Grusin et al. |
| 2003/0014119 A1 | 1/2003 | Capon et al. |
| 2003/0074078 A1* | 4/2003 | Doubler et al. .......... 623/22.42 |
| 2003/0088316 A1 | 5/2003 | Ganjianpour |
| 2003/0149486 A1* | 8/2003 | Huebner .................. 623/19.11 |
| 2003/0149487 A1 | 8/2003 | Doubler et al. |
| 2003/0204268 A1* | 10/2003 | Gerbec et al. ............ 623/23.44 |
| 2003/0204269 A1* | 10/2003 | Gerbec et al. ............ 623/23.47 |
| 2004/0117024 A1* | 6/2004 | Gerbec et al. ............ 623/18.11 |
| 2004/0122525 A1* | 6/2004 | Daniels et al. ........... 623/22.42 |
| 2005/0004679 A1* | 1/2005 | Sederholm et al. ....... 623/22.42 |
| 2006/0052877 A9* | 3/2006 | Doubler et al. .......... 623/22.42 |
| 2007/0005146 A1 | 1/2007 | Heyligers et al. |

FOREIGN PATENT DOCUMENTS

| | | |
|---|---|---|
| WO | WO 98/08468 A1 | 3/1998 |

OTHER PUBLICATIONS

European Search Report for Application No. EP 04 81 0479, dated Sep. 27, 2007, 3 pages.

* cited by examiner

MODULAR CANNULATED TOTAL JOINT PROSTHESIS

FIELD OF THE INVENTION

The present invention relates to a joint prosthesis, such as a hip or shoulder joint prosthesis. In particular, the invention relates to a modular joint prosthesis having a replaceable shaft.

BACKGROUND OF THE INVENTION

In the field of orthopaedics, prostheses have been devised for the replacement of many joints in the body. Common applications include hip, shoulder, and knee joint replacements. Such total joint replacement has become a commonplace and effective treatment for the incapacitating pain of arthritis for example.

A large joint prosthesis, such as for a hip or shoulder, typically includes a head that serves as the ball joint and a stem having a shaft that is inserted into a long bone to fix the prosthesis in place. The head and stem and the methods of attaching the head to the stem will differ depending on the type of joint to be replaced and the particular prosthesis as is known in the art.

In a conventional arthroplasty procedure, a prosthesis is first selected and assembled. In surgery, an incision is made for access to the long bone, which is prepared for receipt of the stem with the use of various broaches, rasps, and reamers to ensure a proper fit. The stem is inserted into the long bone and fixed into place with cement, screws, or other means known in the art.

On occasion, the long bone adjacent a prosthesis fractures, requiring treatment. Were the prosthesis not in place, such a fracture would conventionally be treated by the insertion of a intramedullary device, such as an intramedullary nail placed across the fracture area and used to fix the bone into place. However, when a joint prosthesis is in place, access to the point of the fracture is more difficult. In such a case, a joint revision may be required, removing the artificial joint and replacing it with another prosthesis that includes a longer stem traversing the fracture. However, such a joint revision is a complicated procedure and is not an ideal methodology. Therefore, a makeshift internal fixation may be performed that attempts to treat the fracture with external devices such as plates, screws, and wires. Another approach to treating the fracture and avoiding joint revision is to utilize bed rest and traction.

It would be advantageous to have a joint prosthesis that is designed to anticipate the possibility of a periarticular fracture above or below the prosthesis and allow effective treatment of the fracture without requiring removal of the entire artificial joint. It would be further advantageous if a joint prosthesis were designed to allow the replacement of the shaft portion of the stem with a different shaft after the prosthesis has been implanted.

It would be desirable to provide a system and/or method that provides one or more of these or other advantageous features. Other features and advantages will be made apparent from the present specification. The teachings disclosed extend to those embodiments that fall within the scope of the appended claims, regardless of whether they accomplish one or more of the aforementioned needs.

SUMMARY OF THE INVENTION

The invention relates to a joint prosthesis for implantation in a patient. The joint prosthesis includes a stem having a proximal portion coupled to the head and a distal portion configured to extend into a long bone of the patient. The distal portion may be removed from the stem after implantation of the prosthesis without also removing the proximal portion.

The invention further relates to a joint prosthesis for implantation in a patient, the joint prosthesis having a body with a central canal extending therethrough. A shaft is coupled to the body and extends through the central canal. The shaft is interchangeable after implantation of the prosthesis by removing the shaft and replacing the shaft with a replacement shaft without dislodging the body from the patient.

The invention further relates to a method of replacing the shaft of a joint prosthesis having a body and a shaft, after the joint prosthesis has been implanted in a patient. The method includes the steps of creating an access aperture in the patient for access to the joint prosthesis, removing the shaft from the patient without removing the body of the prosthesis, and inserting a replacement shaft into the patient. The method further includes the steps of coupling the replacement shaft to the body, locking the replacement shaft into place in the patient, and closing the access aperture.

Further still, the invention relates to a modular joint prosthesis system. The system includes a body, an articular surface, and a first shaft configured to be coupled to the body. A second shaft is also configured to be coupled to the body and the second shaft is used to replace the first shaft after implantation of the prosthesis into a patient without first removing the body of the prosthesis from the patient.

The invention is capable of other embodiments and of being practiced or being carried out in various ways. Alternative exemplary embodiments relate to other features and combinations of features as may be generally recited in the claims.

BRIEF DESCRIPTION OF THE DRAWINGS

The invention will become more fully understood from the following detailed description, taken in conjunction with the accompanying drawings, wherein like reference numerals refer to like elements, in which.

DETAILED DESCRIPTION OF PREFERRED EMBODIMENTS

Figure 1:
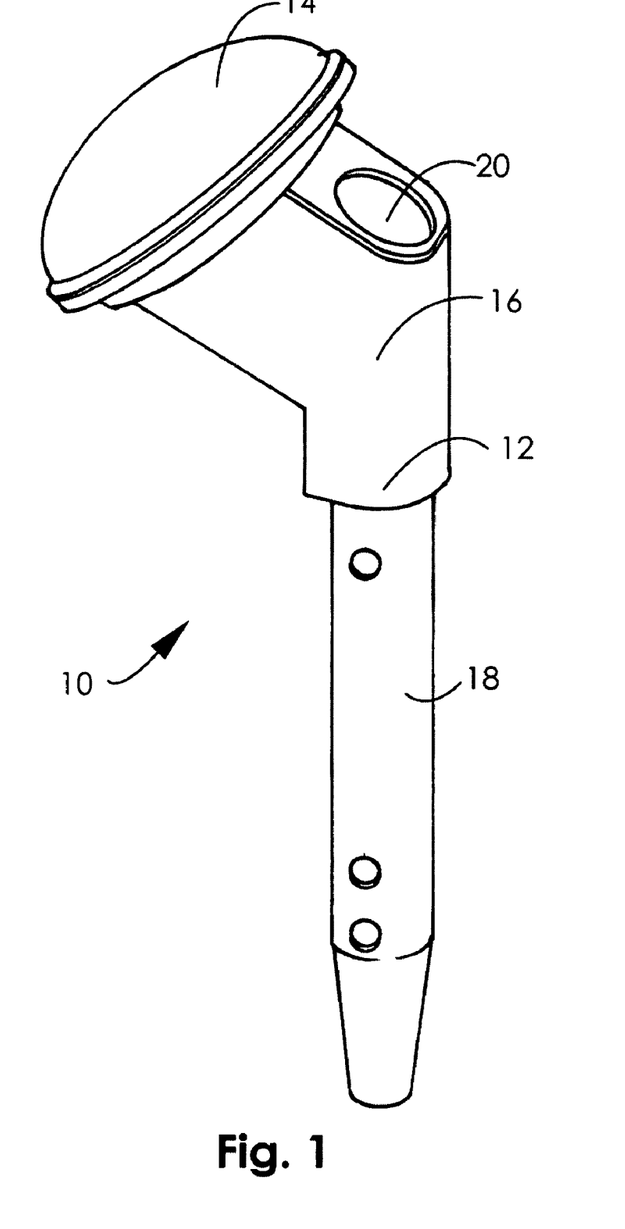
FIG. 1 is a perspective view of a prosthesis according to an exemplary embodiment of the invention.

Referring to FIG. 1, an artificial joint such as a hip or shoulder joint prosthesis is generally shown as prosthesis 10. According to one embodiment, prosthesis 10 includes a stem 12 and a prosthetic head, shown as head 14, attached to the stem 12. The stem 12 has a proximal portion, shown as body 16, and a distal portion, shown as shaft 18. In the embodiment of FIG. 1, head 14 is coupled to body 16, which may be accomplished in one of several ways known in the art.

Figure 2:
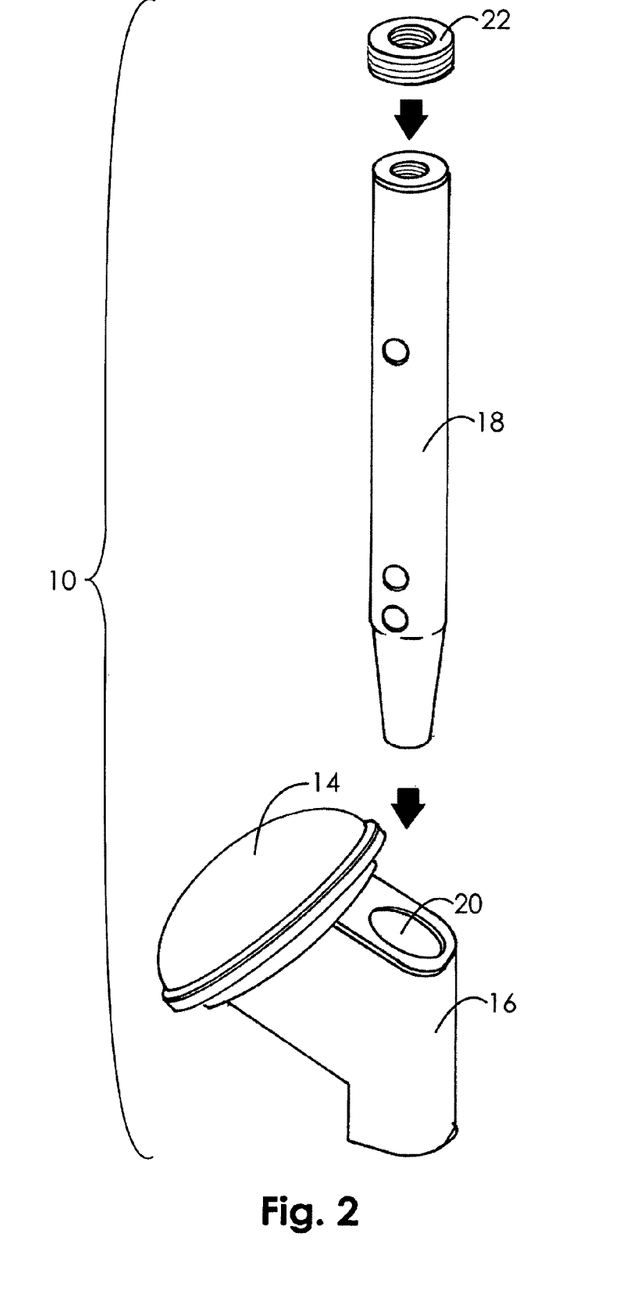
FIG. 2 is an exploded view of the prosthesis of FIG. 1.

Referring to FIG. 2, in an exemplary embodiment, shaft 18 is a separate component from body 16 and is assembled with body 16 via insertion through an aperture, shown as a central canal 20. Depending on the chosen configuration, an insert 22 may be utilized to lock the shaft 18 into place by interlocking with the central canal 20 above the shaft 18. The primary components of the prosthesis 10 may be constructed of titanium or a titanium alloy as is known in the art.

Figure 3:
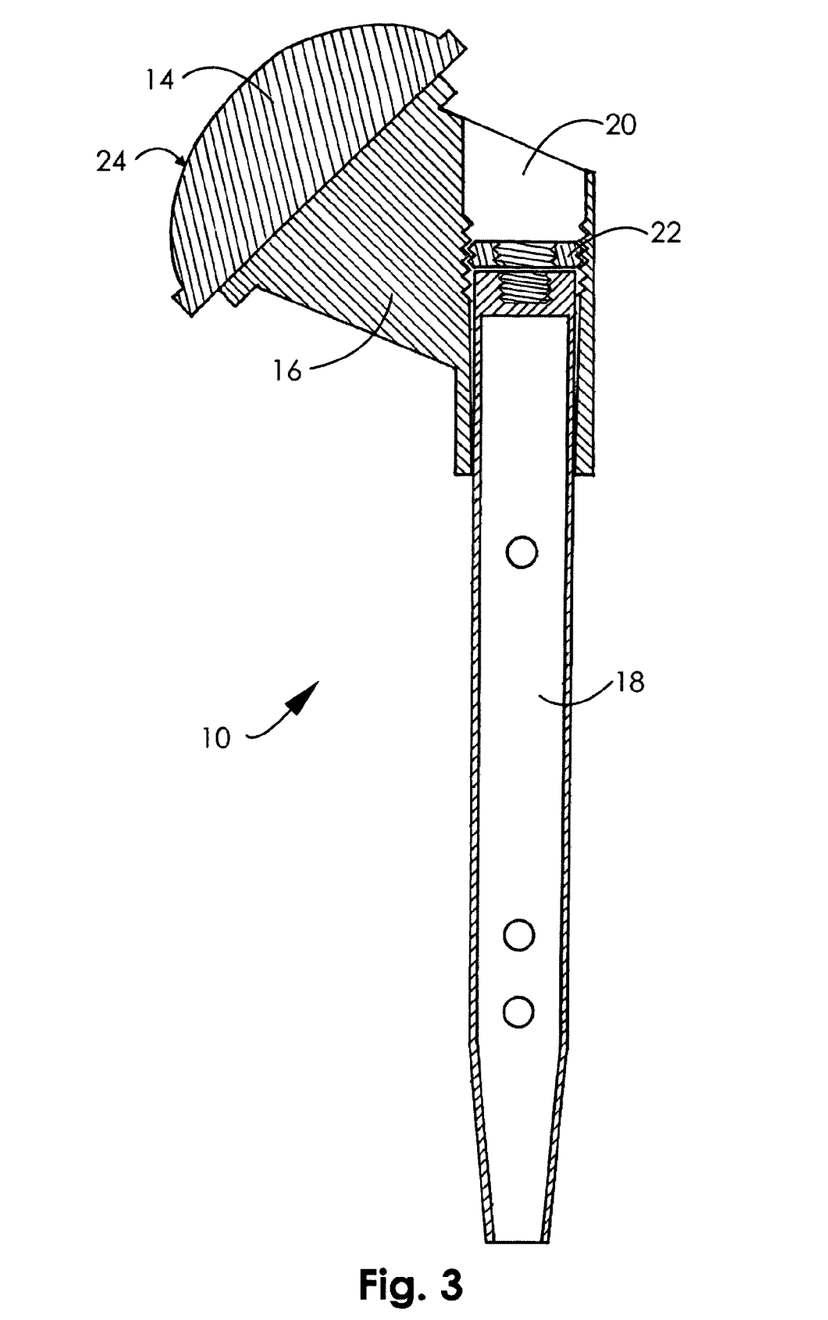
FIG. 3 is a sectional view of the prosthesis of FIG. 1.

Referring to FIG. 3, the shaft 18 may be locked into place in the central canal 20 in a variety of ways known in the art, such as a press-fit or taper lock, such as a Morse taper. While the taper lock prevents further movement of the shaft 18 in a downward direction, the insert 22 may be locked into place in the central canal 20 to prevent upward movement of the shaft 18. Insert 22 may be utilized as a locking element in a variety of ways, such as by screwing the insert 22 into the central canal 20. Ideally, insert 22 is configured to be easily removable, such as by unscrewing insert 22, in order to provide access to shaft 18. Shaft 18 is typically tapered in the proximal to distal direction and the central canal is correspondingly tapered to effectuate the taper lock or Morse taper.

Figure 4:
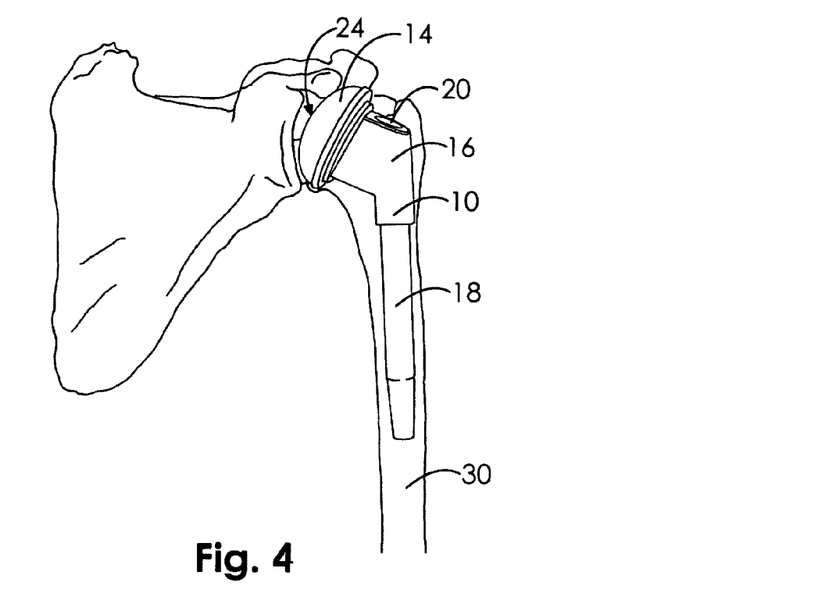
FIG. 4 is a cut-away elevation view of a shoulder joint having a prosthesis implanted into the humerus.

Referring to FIG. 4, prosthesis 10 is shown as implanted into a long bone as a joint replacement. In the embodiment of FIG. 4, the joint is a shoulder joint and the long bone is the humerus 30. The head 14 provides an articular surface 24 intended to mimic the natural articular surface of the long bone in the replaced natural joint. In other embodiments, the articular surface 24 may be provided directly on the body 16 without a separate head attachment.

Prior to implantation of the prosthesis 10 into the humerus 30, the intramedullary canal in the humerus 30 is first reamed to create the appropriate sized cavity for the body 16 and shaft 18. The shaft 18 may be attached to the body 16 prior to implantation, or after the body 16 has already been implanted. Body 16 may have bony in-growth surfaces such as solder beads or mesh that assist in the securing of body 16 within the bone. Due to the modular construction of the prosthesis, the surgeon may select from shafts of various sizes and configurations.

The surgical methods of performing a primary joint arthroplasty are known, including opening an aperture in the patient for access to the joint, preparing the long bone for insertion of the prosthesis, and utilizing bone cement such as methyl methacralate to fix the stem into place. The chosen shaft may be of static size or may be expandable. Depending on the size and method of locking the shaft into place, the insert may be utilized to fill up the remaining portion of the central canal and further lock the shaft into place. While prosthesis 10 is shown as being implanted into a shoulder joint in FIG. 4, the type of prosthesis shown is not intended to be limiting and may also be a hip prosthesis or a prosthesis for other joints in the body, such as the knee.

Figure 5:
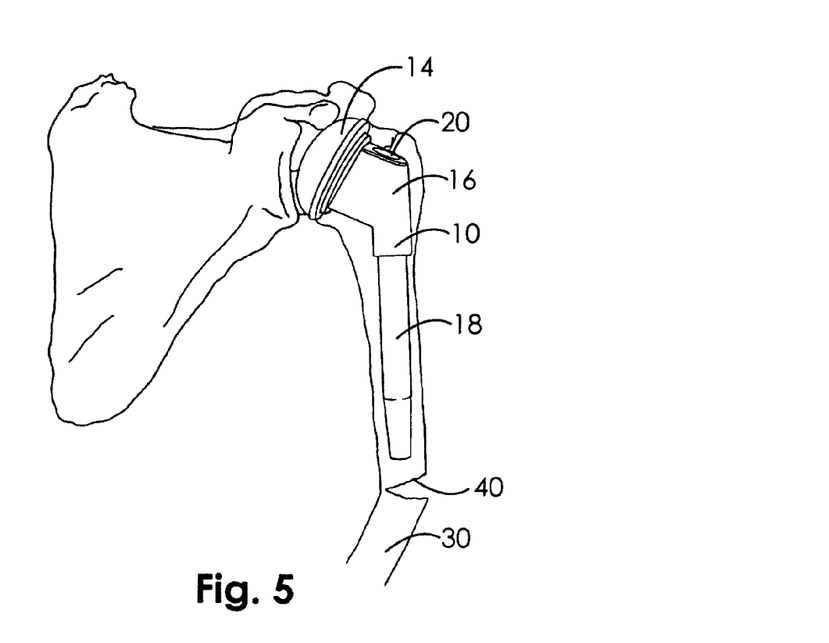
FIG. 5 is a cut-away elevation view of the shoulder joint of FIG. 4 with a fractured humerus.
Figure 6:
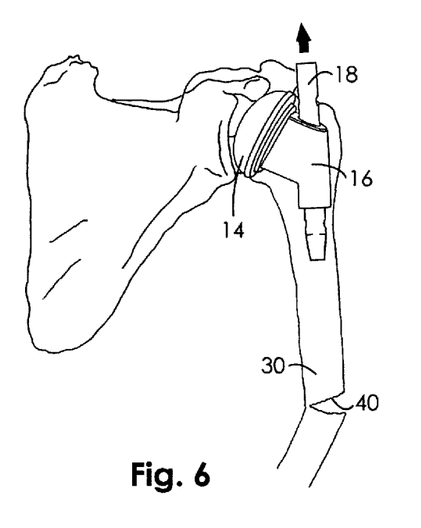
FIG. 6 is a cut-away elevation view of the shoulder joint of FIG. 5 with the shaft partially removed from the prosthesis.

Referring to FIG. 5, sometime after implantation of the prosthesis 10, the patient may suffer from a broken bone or metastatic lesion, shown as fracture 40, that occurs distally to the prosthesis 10. The prosthesis 10 has an advantageous configuration in such a circumstance because the shaft 18 may be removed from the body 16 and replaced with a different shaft or in intramedullary nail without requiring complete joint revision. Instead, referring to FIG. 6, shaft 18 is removed through the central canal 20 without requiring the dislodging or removal of body 16 and head 14.

When necessary, removal of shaft 18 may be accomplished via access through the original arthroplasty incision. If insert 22 was used (see FIG. 3), insert 22 is removed first, followed by shaft 18. A removal device, such as that shown in FIGS. 12-16 may be used to aid in the removal of shaft 18 and/or insert 22. If bone cement was used to secure the shaft 18 in the initial surgery, some work may be required to dislocate shaft 18 from the cement before removing it through the central canal. In the embodiment depicted in FIG. 6, the shaft 18 is removed in the reverse direction of its original insertion into the central canal 20 as indicated by the arrow.

Figure 7:
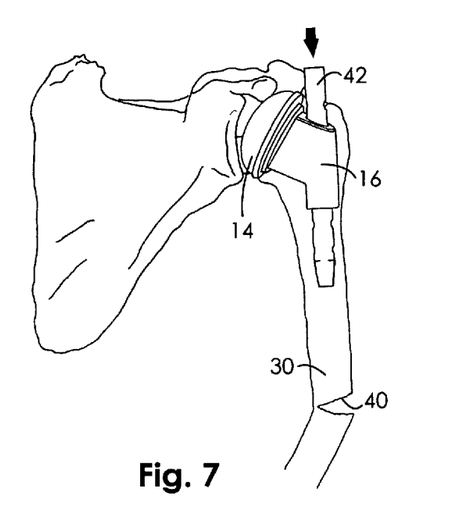
FIG. 7 is a cut-away elevation view of the shoulder joint of FIG. 5 with a replacement shaft for the prosthesis partially inserted therein.

Referring to FIG. 7, a replacement shaft may be selected that serves the dual purposes of securing the artificial joint and treating the fracture 40. In the embodiment of FIG. 7, an intramedullary nail has been selected as the replacement shaft for treatment of the fracture 40, the intramedullary nail being longer than the original shaft 18 such that it will extend across the fracture 40.

Prior to insertion of the replacement shaft 42, it may be necessary to drill out the cement used in the original joint replacement surgery including any cement restrictor that may have been used. The replacement shaft 42 is then inserted through the central canal as shown by the arrow in FIG. 7, and coupled to the body 16 via the press-fit or taper lock between the replacement shaft 42 and body 16. Other approaches to locking the replacement shaft 42 in place may also be used. Because the body 16 is not replaced, the replacement shaft 42 may have a similar configuration to the original shaft 18 at the proximal end for locking purposes. The removal device shown in FIGS. 12-16 may be used to aid in the insertion process according to an exemplary embodiment.

Figure 8:
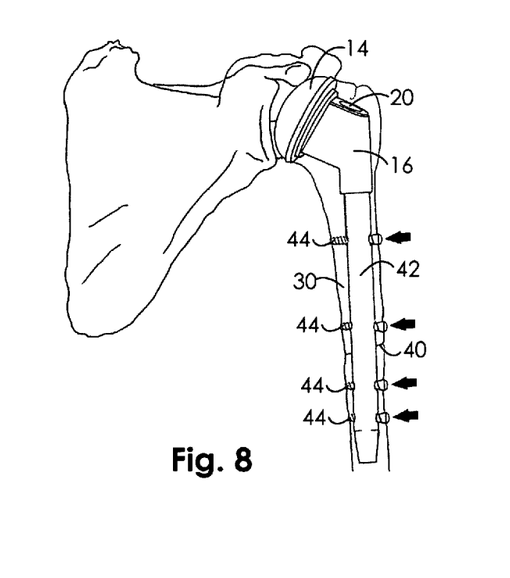
FIG. 8 is a cut-away elevation view of the shoulder joint of FIG. 5 with a replacement shaft inserted in the prosthesis across the fracture site.

Referring to FIG. 8, after the replacement shaft 42 has been inserted into place, it may be secured by cross screws 44 that extend through the humerus 30 and replacement shaft 42. An insert (not shown, which may be the same or similar to insert 22) may be utilized to fill remaining space in the central canal 20 and further lock the replacement shaft 42 into place. Tension anchors or tension screws may serve the function of cross screws 44 and additional bone cement may be utilized to secure replacement shaft 42 into place.

Figure 9:
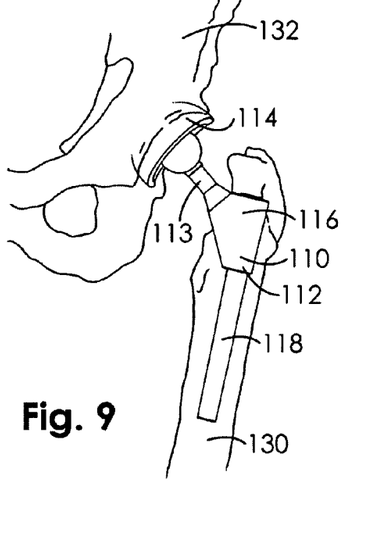
FIG. 9 is a cut-away elevation view of a hip joint having a prosthesis implanted in the femur.

Referring to FIG. 9, according to another embodiment of the invention, a prosthesis 110 intended for use as a femoral prosthesis includes a stem 112 and a head 114. The head 114 may be attached to the stem 112 via a neck 113. The stem 112 includes a body 116 and a shaft 118. The stem 112 is implanted in a femur 130 according to a hip arthroplasty procedure known in the art. The head 114 replaces the original joint between the femur 130 and the hip bone 132.

Further referring to FIG. 9, prosthesis 110 has a similar construction to the prosthesis 10 described above in that the shaft 118 is intended to be replaceable after implantation of the prosthesis 110 by removing the shaft 118 via central canal 120 if necessary and replacing the shaft with an alternate or replacement shaft.

Figure 10:
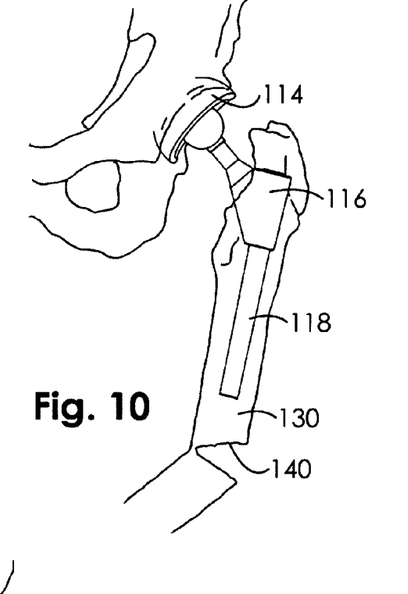
FIG. 10 is a cut-away elevation view of the hip joint of FIG. 9 with a fractured femur.
Figure 11:
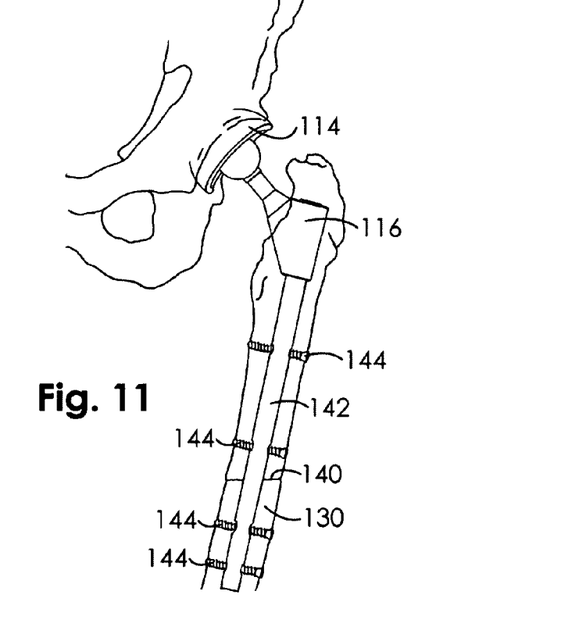
FIG. 11 is a cut-away view of the hip joint of FIG. 9 with a replacement shaft extending across the fracture site.

Referring to FIGS. 10 and 11, in the event of a fracture 140 or metastatic lesion requiring treatment distal to the prosthesis 110, the original shaft 118 may be removed without removing or displacing the body 116 and be replaced with a replacement shaft 142 that preserves the function of the prosthesis 110 while also permitting treatment of the fracture 140. In the embodiment depicted in FIG. 11, the replacement shaft 142 is an intramedullary nail utilizing cross screws 144 to fix the intramedullary nail with respect to the long bone or femur 130. Removal and replacement of the shaft 118 may be accomplished in a similar fashion to the procedure described above with reference to FIGS. 6 and 7.

Figure 12:
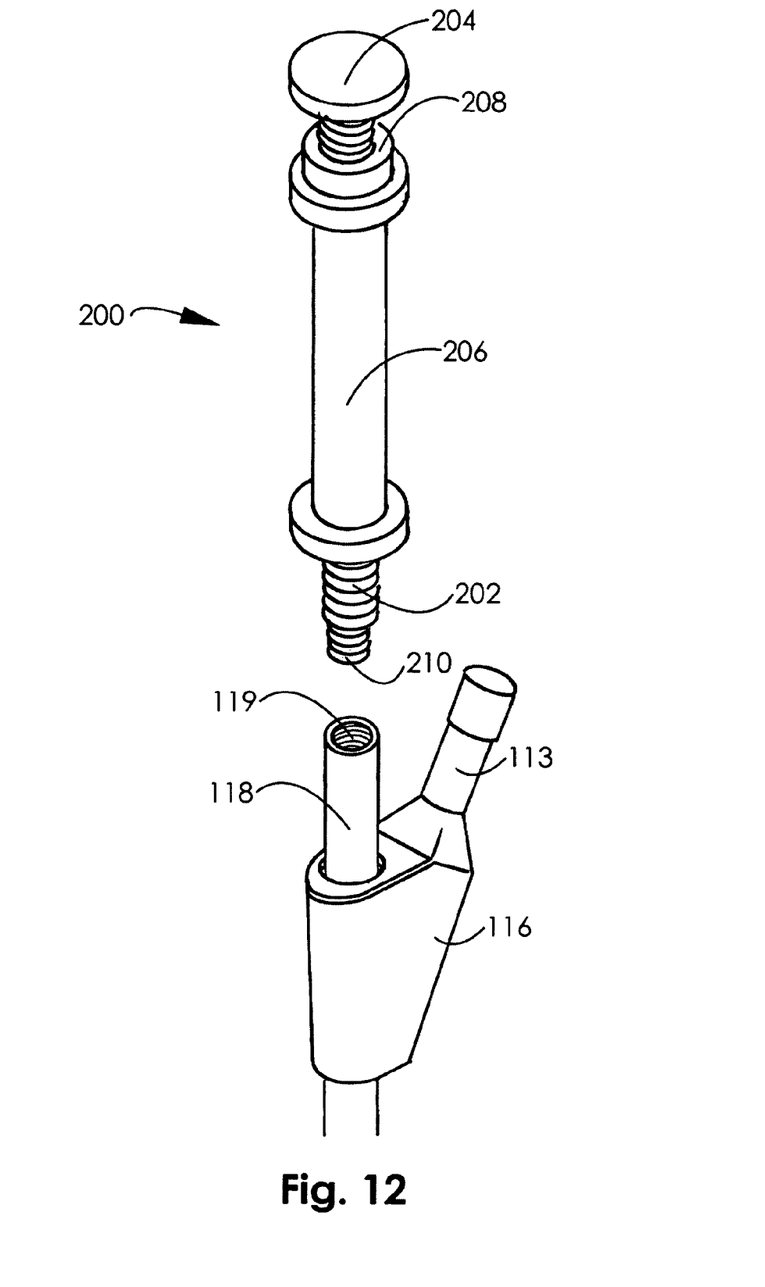
FIG. 12 is a perspective view of a shaft removal device disconnected from the shaft of a prosthesis.

Referring to FIG. 12, a shaft removal device, shown as remover 200, may be utilized to aid in the removal and replacement of a prosthesis shaft, shown as shaft 118. In an exemplary embodiment, remover 200 includes a threaded rod 202 having a head 204 on one end and a jacket 206 configured to be adjustably threaded onto the rod 202. A nut 208 may be used to secure the jacket 206 at a desired location. On the distal end of threaded rod 202 is a shaft interface 210 intended to be coupled to shaft 118 for removal purposes. In the embodiment shown in FIG. 12, a portion of prosthesis 110 is shown, including body 116 and neck 113. However, the remover 200 is intended for use with many designs of replaceable shaft prostheses and is not limited to use with the particular prosthesis embodiment that is shown.

Figures 13, 14:
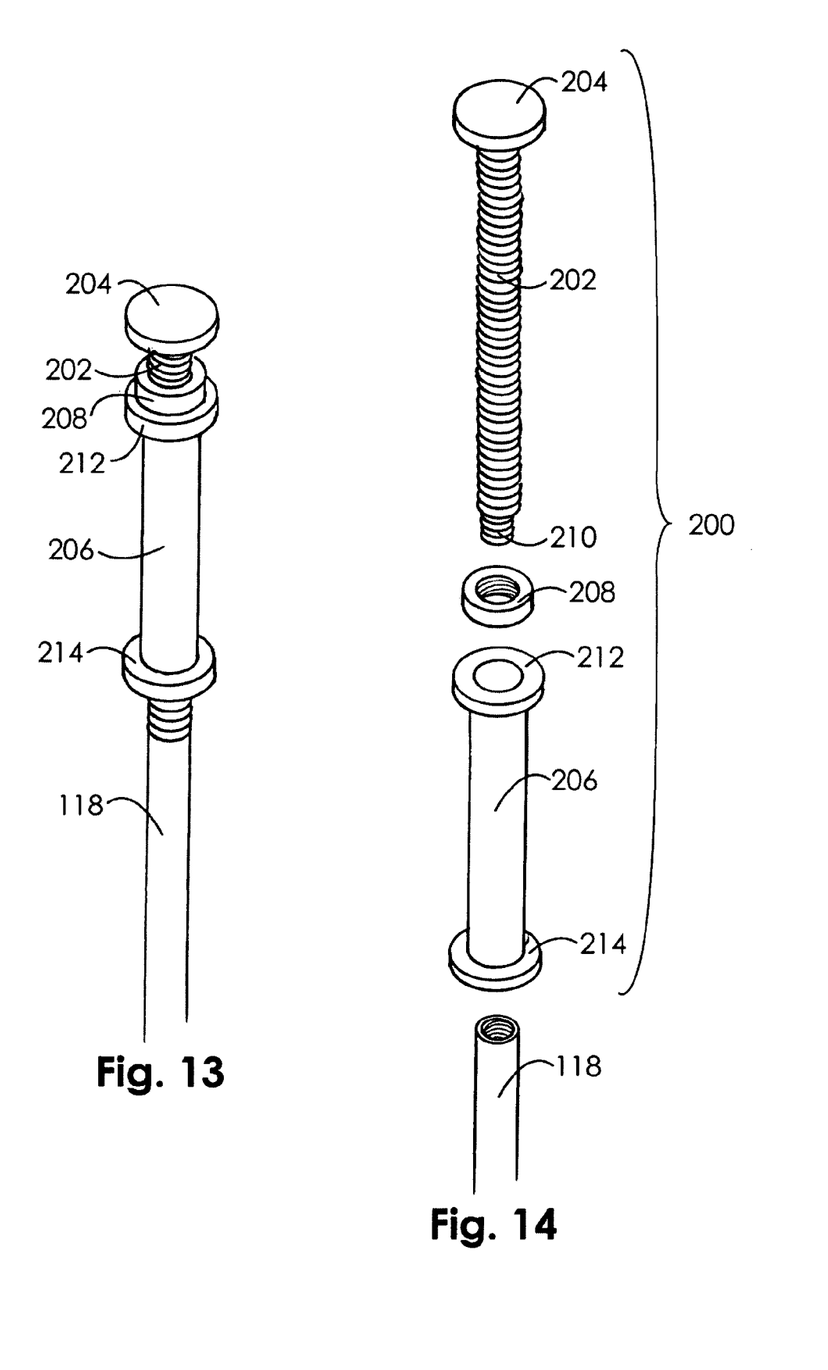
FIG. 13 is a perspective view of a shaft removal device connected to the shaft of a prosthesis.
FIG. 14 is an exploded perspective view of the shaft removal device of FIG. 13.

Referring to FIG. 13, the threaded rod 202 may be screwed into the shaft 118, thus permitting the surgeon to utilize the head 204 and jacket 206 as a handle to aid in removing shaft 118. Without remover 200, it may be difficult to grasp and remove the shaft 118 from the long bone into which it is implanted. Jacket 206 is shown as having a pair of flanges 212, 214. Nut 208 may be tightened against flange 212 in order to lock jacket 206 into place with respect to threaded rod 202.

Figure 15:
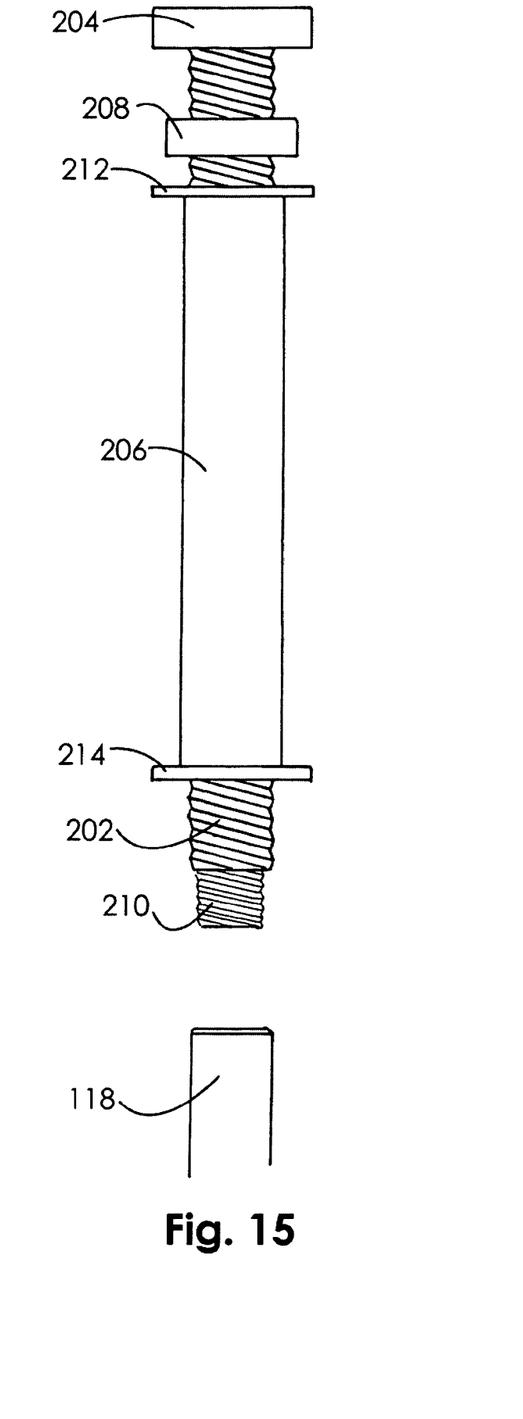
FIG. 15 is an elevation view of a shaft removal device and the shaft of a prosthesis.
Figure 16:
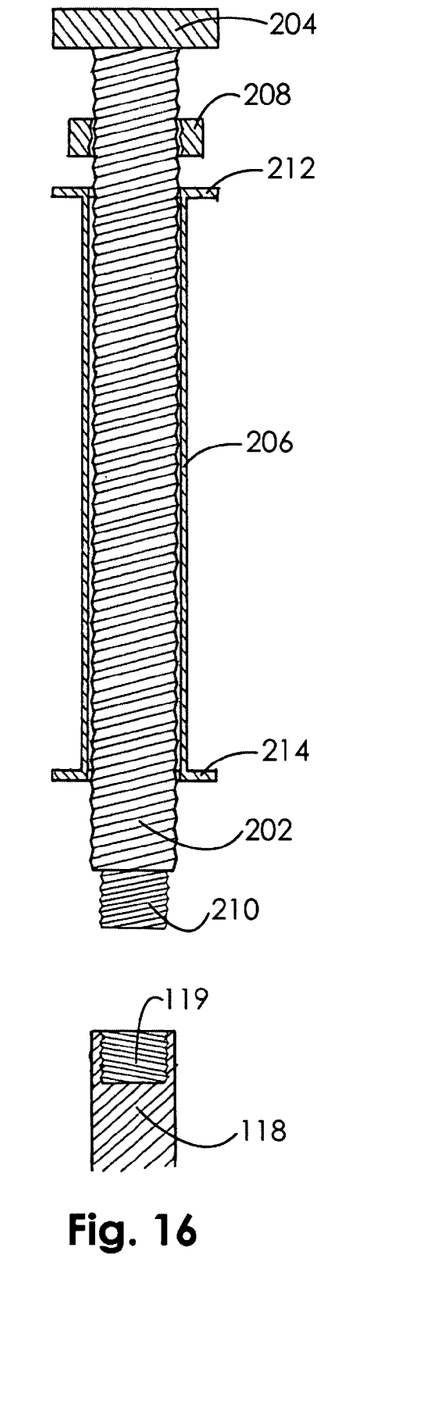
FIG. 16 is a sectional view of the shaft removal device of FIG. 15.

Referring to FIGS. 14-16, in an exemplary embodiment, shaft 118 has a threaded recess 119 that is sized to receive a shaft interface 210 at the distal end of threaded rod 202. The shaft interface 210 may be a portion of the rod 202 that is of a smaller diameter than the remaining portion of the threaded rod 202. Further, the remover 200 may also be configured to attach to an insert (such as insert 22 shown in FIG. 3) that has threads corresponding to the threaded rod 202. Depending on the configuration of the shaft and/or insert, the user may change the location of jacket 206 on the threaded rod 202, as needed, such as by rotating jacket 206 along the threads of threaded rod 202 before securing jacket 206 with nut 208.

Because the prostheses described herein provide for the removal and replacement of the shaft without requiring complete joint revision including the displacement and removal of the body portion of the stem, greater flexibility over conventional designs with respect to the treatment of later developing fractures or metastatic lesions is afforded. The prostheses described herein anticipate the potential problem of a periarticular fracture above or below an existing prosthesis by the desired approach of utilizing an intramedullary device or longer distal portion of the stem rather than conventional approaches of complete joint revision, makeshift internal fixation, or bed rest and traction.

While the detailed drawings and specific examples given herein describe various exemplary embodiments, they serve the purpose of illustration only. It is to be understood that the invention is not limited in its application to the details of construction and the arrangements of components set forth in the preceding description or illustrated in the drawings. For example, although hip and shoulder joint prostheses are described, the modular cannulated concept described herein may be applied to prostheses for other joints in the body that would derive benefit from the system described herein. Furthermore, other substitutions, modifications, changes, and omissions may be made in the design, operating conditions, and arrangements of the exemplary embodiments without departing from the scope of the invention as expressed in the appended claims.

What is claimed is:

1. A method of replacing a shaft of a joint prosthesis having a body, a head, and a shaft after the joint prosthesis has been implanted in a patient, wherein the body is coupled to the head and the shaft has an outer surface adapted to interface with an intramedullary canal of the patient, comprising:
   creating an access aperture in the patient for access to the joint prosthesis;
   removing the shaft from the patient without removing both the body and the head from the patient and without decoupling the head from the body;
   inserting a replacement shaft into the patient;
   coupling the replacement shaft to the body without removing both the body and the head from the patient and without decoupling the head from the body;
   locking the replacement shaft into place in the patient; and
   closing the access aperture.

2. The method of claim 1, wherein the body has an aperture configured to receive the shaft or the replacement shaft and wherein the coupling step includes inserting the replacement shaft into the aperture of the body.

3. The method of claim 2, further comprising coupling an insert to the body, the insert extending at least partially into the aperture of the body.

4. The method of claim 1, wherein the replacement shaft is an intramedullary nail.

5. The method of claim 1, wherein the replacement shaft is longer than the shaft.

6. The method of claim 1, wherein the body includes a central canal that extends through the body, and further wherein the step of removing the shaft includes accessing the shaft via an end of the central canal nearest the head.

7. The method of claim 6, wherein the step of coupling the replacement shaft includes inserting the replacement shaft into the central canal via an end of the central canal nearest the head.

8. The method of claim 1, further comprising selecting a replacement shaft longer than the shaft such that the replacement shaft extends across a fracture in a bone of a patient, the fracture located distally from the distal end of the shaft.

* * * * *